United States Patent

Edenbaum et al.

[11] Patent Number: 5,258,036
[45] Date of Patent: Nov. 2, 1993

[54] BODY PART MOLD AND METHOD OF MAKING

[75] Inventors: Martin Edenbaum, Princeton Junction, N.J.; Tripp A. Murr, Broken Arrow; Gary W. Silvers, Tulsa, both of Okla.

[73] Assignee: Carapace, Inc., Tulsa, Okla.

[21] Appl. No.: 820,938

[22] Filed: Jan. 15, 1992

[51] Int. Cl.⁵ ............................ A61F 2/78; B29C 33/40
[52] U.S. Cl. ........................... 623/33; 264/222; 264/DIG. 30
[58] Field of Search .................... 623/33, 66, 901, 35, 623/36; 602/8, 62; 264/222, DIG. 30, 223

[56] References Cited

U.S. PATENT DOCUMENTS

| | | | |
|---|---|---|---|
| 1,351,789 | 9/1920 | Rowley | 264/DIG. 30 X |
| 1,907,511 | 5/1933 | Davies | 623/33 |
| 3,520,002 | 7/1970 | Wellington | 264/222 X |
| 3,962,395 | 6/1976 | Hagglund | 264/222 X |
| 4,019,506 | 4/1977 | Eschmann | 602/8 |
| 4,502,479 | 3/1985 | Garwood et al. | 602/8 |
| 4,628,917 | 12/1986 | Campagna et al. | 602/8 |

FOREIGN PATENT DOCUMENTS 2539616  7/1984  France .................. 623/35

Primary Examiner—Randall L. Green
Assistant Examiner—D. Willse
Attorney, Agent, or Firm—Head & Johnson

[57] ABSTRACT

Method and materials for making a mold that conforms to a body part, such as the stump of an amputated limb. This is formed by two, or more, layers of knit fabric substrate, one or more of which is impregnated with a water activated foaming isocyanate polymer casting resin which is placed over the body part to be molded, and allowed to cure.

6 Claims, 2 Drawing Sheets

BODY PART MOLD AND METHOD OF MAKING

BACKGROUND OF THE INVENTION

Field of the Invention

This invention relates to the field of making molds or casts that conform to the shape of a body part, or to the stump of an amputated member. More specifically, this relates to molds which are made of casting resin and which may be used to make a negative mold from which a custom fit orthotic or prosthetic device may be fashioned.

Description of the Related Art

Molds or casts of body parts are used for various purposes. Molds of the face are often taken to make masks, or decorative items (U.S. Pat. No. 4,828,116). Molds of the feet may be used to form arch supports or orthopedic footwear (U.S. Pat. No. 4,006,542). Molds of a breast may be used to form a prosthesis after the breast is surgically removed (U.S. Pat. No. 4,086,666). Molds of other body parts have been described: fingers/fingernails (U.S. Pat. No. 4,361,160); scalp (U.S. Pat. No. 3,889,695); head/knee/groin/ear/breast (U.S. Pat. No. 4,006,542); feet/hands/face (U.S. Pat. No. 4,828,116). Perhaps the largest use of such molds is with amputated limbs (U.S. Pat. Nos. 4,225,982; 4,696,780; 4,923,474; 5,004,477). A mold of the "stump" of the amputated member is taken (forming a "negative" mold), and then used to cast a replica of the "stump" (a "positive" reproduction) which can then be used to fashion and fit a prosthesis for the amputated limb.

Prior methods have generally used plaster of Paris as the casting material to form such molds. This is usually applied as multiple strips of material impregnated with plaster of Paris, each of which must be soaked. This is time consuming and very messy. The plaster of Paris takes a long time to set (10 to 30 minutes or more), and complete drying may take up to 72 hours. The wet plaster of Paris must thus remain on the body part for a considerable period before it can be removed. The damp plaster is very weak and fragile when removed. Some patients may have difficulty remaining still for this extended period which may be uncomfortable for the patient. The prolonged setting time also causes loss of resolution in the mold--over a period of time, small body movements cause distortion or "blurring" of the mold surface, with loss of fine details. Plaster of Paris molds also tend to be heavy, to break easily and are subject to chipping.

Some applications have used alginate (U.S. Pat. No. 4,361,160 and 4,828,116) to form molds. The part to be molded must be immersed in a container of alginate and water. Thus the mold is large and heavy and not all body parts are amenable to immersion. It may be difficult for a patient to move into a position to immerse the stump. The application is messy and requires various sizes of containers. Alginate is not available in substrate impregnated strips. Special mixers are often required for the alginate-water mixing, to eliminate air bubbles. The alginate molds are initially rubbery in texture. After prolonged periods they become very hard, and distorted due to water loss. Thus, they are not suitable for long term storage.

Some processes use heat deformable plastic (U.S. Pat. No. 4,783,293 and 4,006,542) to form an impression of a body part.

SUMMARY OF THE INVENTION

It is an object of this invention to provide a method and apparatus for making a mold of a body part which will have high resolution for fine details.

It is another object of this invention to provide a method and apparatus for making a mold of a body part that is easy and rapid to form and apply with a minimum of mess.

It is yet another object of this invention to provide a method and apparatus for making a mold of a body part that is sturdy, durable and light.

It is still a further object of this invention to provide a method and apparatus for making a mold of a body part that will set rapidly and be ready for removal and use within a few minutes.

It is another object of this invention to provide a mold that may be stored for prolonged periods.

It is yet another object of this invention to provide a method and apparatus for making a mold that uses a foaming synthetic casting resin.

In the embodiment of this invention which is used to make molds of amputation stumps, the mold comprises a tubular shaped knit stretchable dry fabric sleeve fitted snugly over the stump. The dry sleeve is then covered with at least one layer of casting material which is another similar sleeve impregnated with a foaming casting resin which has been activated by wetting. Examples of casting resin and substrate are exemplified in U. S. Pat. Nos. 4,411,262; 4,442,833; 4,502,479--the contents of these patents are incorporated herein by specific reference. In the embodiments tested, both one casting layer and two casting layers have been used. The wetted casting layer(s) is firmly molded over the dry body contact layer to conform to the shape of the stump and allowed to cure. The mold is then removed from the stump. This is now a "negative" mold of the stump. The negative mold may be used to cast a "positive" impression. This positive impression may be used to fit the cup of a prosthesis.

These objects are meant to be illustrative and not limiting. The manner of operation, novel features and further objectives and advantages of this invention may be better understood by reference to the accompanying drawings, description and claims.

DESCRIPTION OF THE PREFERRED EMBODIMENT

Figure 1:
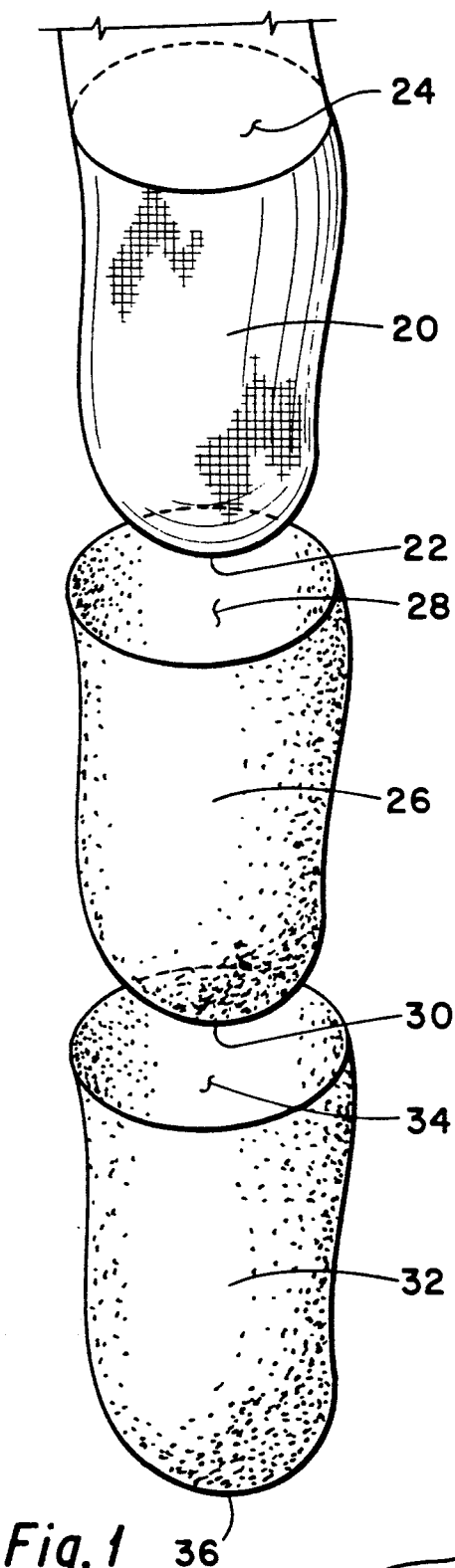
FIG. 1 is an exploded view of a three-layer molding device.

FIG. 1 illustrates, in an exploded view, a mold with three layers. The skin contact layer 20 is formed of stretchable or elastomeric material that is stretchable in at least two dimensions. It has been found that a knit fabric formed of a material such as polyester, polypropylene or the like, works well. It is important that the material be formed of high tensile strength fibers, so that it can be snugly fitted and stretched over the body part from which a mold is to be made, without tearing. When applied to amputation stumps, a tubular construction is used with one end closed 22 and one end open 24. Various sizes may be made. The general outline of the skin contact layer 20, when applied, as shown in FIG. 1, conforms to the shape of an underlying amputation stump (not shown). The stump may be coated (prior to applying the skin contact layer 20) with oil, vaseline, or the like, to facilitate removal of the cured mold. The open end 24 of the tubular skin contact layer 20 is slid over the amputation stump until the closed end 22 contacts the end of the stump. The skin contact layer 20 is smoothed and stretched over the stump to form a smooth closely fitting layer without wrinkles.

After the skin contact layer 20 is applied a first tubular casting layer 26 is then fitted over the skin contact layer 20. This first casting layer 26 is similar to the skin contact layer 20 but has been coated and/or impregnated with a casting resin. The resin is activated by water. The first casting layer 26 is thus wetted, and its open end 28 slipped over the skin contact layer 20 that is already on the stump, until the closed end 30 is snug against the end of the stump. The casting member is smoothed over the skin contact layer 20 so as to conform closely to the underlying stump.

A second wetted tubular casting layer 32 may be slipped over the first casting layer 26 by fitting the open end 34 of the layer 26 over the underlying layers 20 and 26 until the closed end 36 is snugly in contact with these layers. All of the layers 20, 26, 32 are then smoothed to the underlying stump to assure a close fit. This is allowed to cure (usually 3-5 minutes) and then removed.

The device may be made of two layers 20 and 26. It may also be made of three, or more layers, as needed. The casting resin tested is an isocyanate (see U.S. Pat. No. 4,502,479). By omitting all, or a large percentage, of the antifoaming agents (silicone compounds, as described in U.S. Pat. No. 4,502,479, which is incorporated herein by reference), the casting resin will foam. This foaming action of the resin, when confined between the layers 20 and 26, forces the resin against the skin contact layer 20 and pushes it into intimate contact with the skin of the stump so that fine detail is captured. Thus, the foaming action causes the activated casting resin to swell and push against the underlying body part. The foaming action also forces the casting material into the dry spaces and interstices of the skin contact layer 20 which joins it to the casting layer and further molds it to the underlying body part. The person applying the mold also runs his or her hands firmly over the external surfaces of the layers which further conforms all of the layers to the underlying body part, and which helps to force the wet casting material into the spaces of the skin contact layer. By forcing casting material against the dry skin contact layer, and into the dry skin contact layer, the skin contact layer becomes integrated with the casting layer(s) and a unitary mold is formed. Other suitable casting resins or other casting materials may be used.

Figure 2:
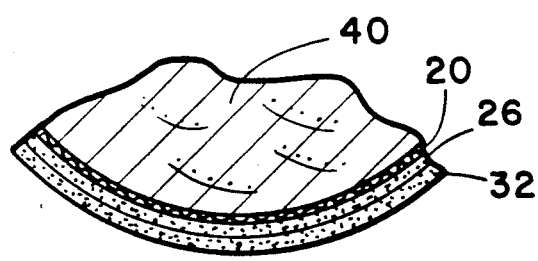
FIG. 2 is a cross-sectional view of a three-layer mold.

FIG. 2 illustrates a portion of the above described three layer mold in partial cross section. The amputation stump is shown generally at 40. The skin contact layer 20, first casting layer 26 and second casting layer 32 are shown.

Figure 3:
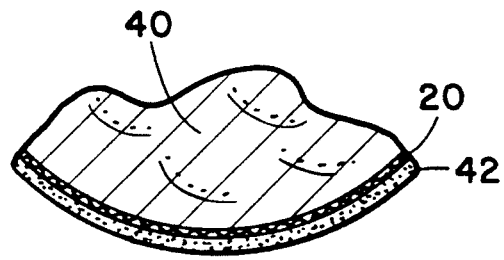
FIG. 3 is a cross-sectional view of a two-layer mold.

FIG. 3 illustrates a two layer embodiment of the above in partial cross section. The amputation stump 40 is covered by a skin contact layer 20 and a single casting layer 42. When a single casting layer is used it may be necessary to use a heavier substrate fabric to retain more resin.

Figure 5:
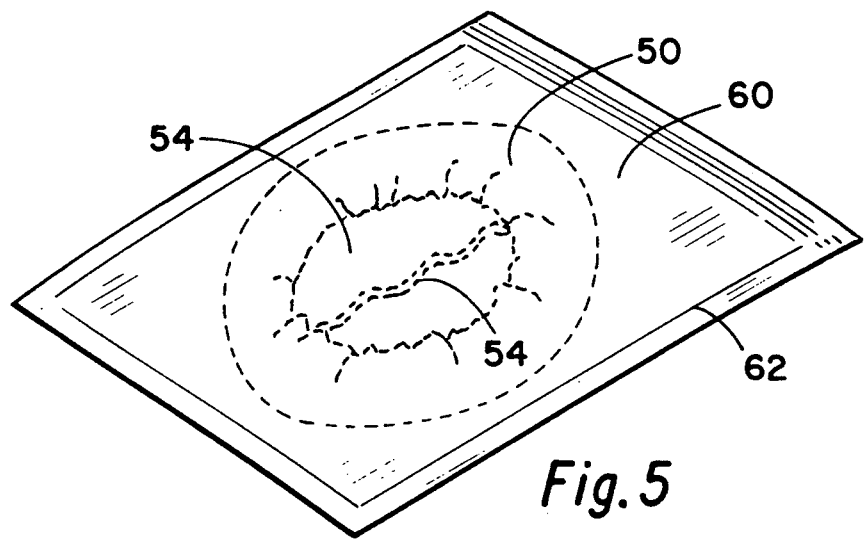
FIG. 5 is a perspective view of a rolled casting layer in a sealed pouch.
Figure 4:
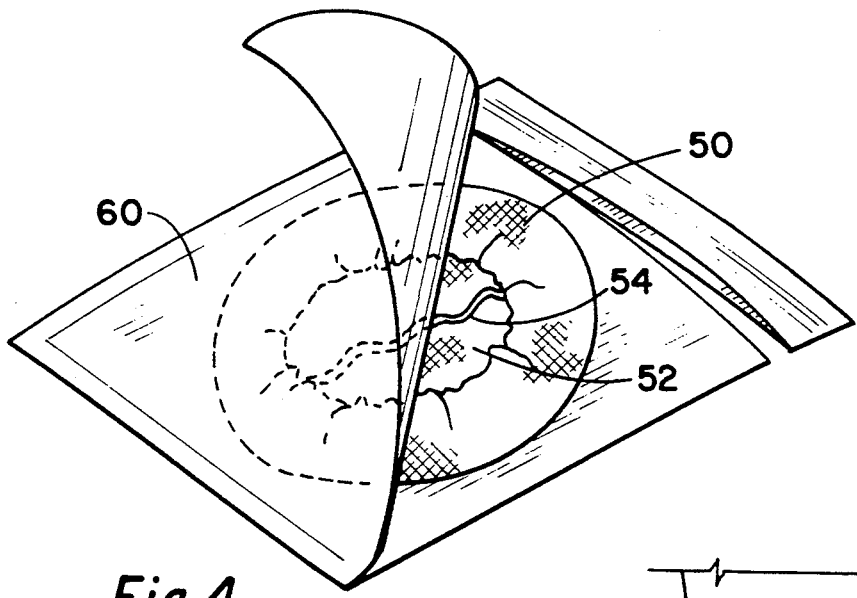
FIG. 4 is a perspective view of a rolled casting layer in a partially opened pouch.

FIG. 4 illustrates One of the fabric layers such as 20, 26 or 32 prior to using, in a partially opened package 60 as described in FIG. 5. The tubular fabric has been rolled into a shape resembling a "condom" with rolled fabric at the edge 50 and the closed end 52 stretched between the edges 50. In the embodiment shown, the closed end 52 has been formed by sewing the end closed, thus forming a seam 54.

FIG. 5 illustrates one of the layers 20, 26, or 32 in a sealed package 60. This is sealed around the edges 62. Layers containing resin must be kept moisture free until use; they may be stored in a pouch 60 formed of foil, moisture impervious plastic, or other suitable material and sealed until needed. Rolled tubular fabric layers are prepackaged in these pouches 60 for convenient use. For the skin contact layer 20, which does not contain resin, the pouch 60 does not have to be moisture impervious. The rolled layer is shown in outline within the pouch 60, with the rolled edge 50, closed end 52 and seam 54, all illustrated.

Figure 6:
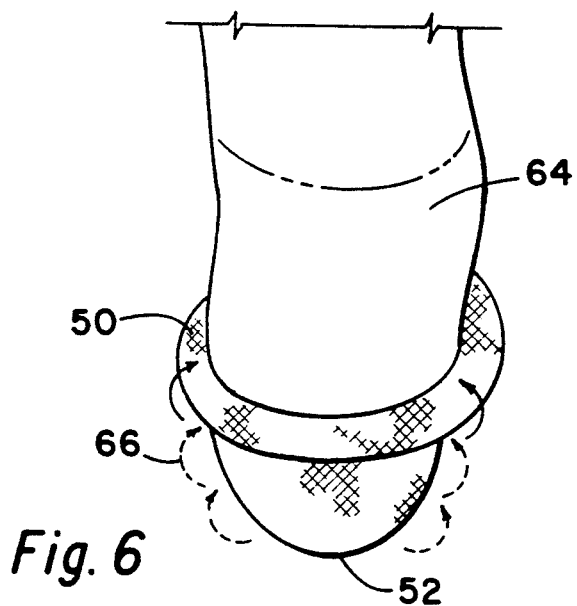
FIG. 6 is a perspective view of an amputation stump being fitted with a rolled layer.

FIG. 6 illustrates one of the rolled layers (from FIG. 4) being applied to an amputation stump 64. The closed end 52 of the layer is applied to the end of the amputation stump, and the rolled edges 50 are rolled up the stump 64 as shown by the arrows 66 in the figure. If this is one of the casting layers, it is wetted with water prior to application, to initiate setting of the resin. If this is the first/inner skin contact layer, it is applied as a dry layer, and the casting layer(s) are then applied over it. As described above, all of the layers are smoothed firmly to the underlying body part to eliminate wrinkles and to create a finely detailed mold of the part.

Figure 7:
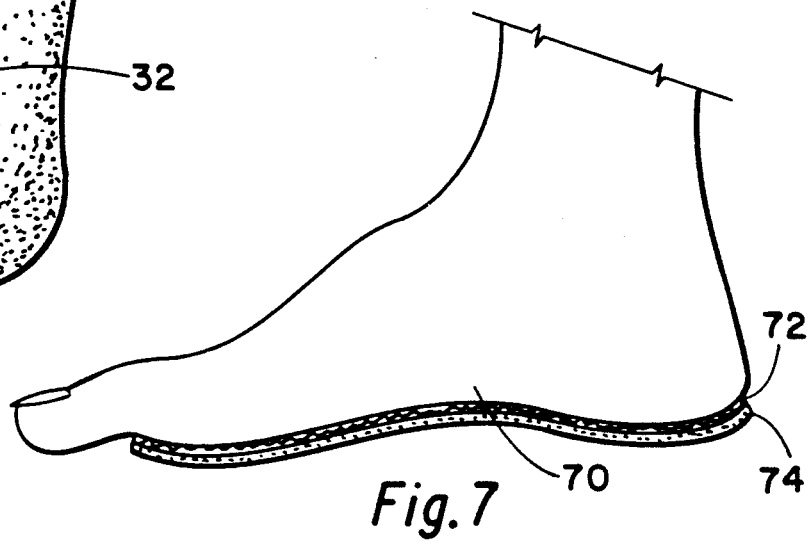
FIG. 7 is a sectional view of a human foot with a mold on the sole of the foot.

FIG. 7 illustrates another embodiment. A mold applied to the sole of a foot 70 is shown and comprises a two layer mold, with a skin contact layer 72 and a casting layer 74. For this embodiment, a flat layer of fabric 72 (rather than the tubular fabric described above) is applied to the body surface to be molded. A similar sized flat layer of wetted casting material 74 comprising fabric impregnated with resin, or other suitable casting material, is then applied to the skin contact layer 72 and allowed to cure. The flat layers may be held against the bottom of the foot, or other body part, by wrapping with an Ace bandage until the casting layer sets. As noted above, various numbers of layers may be used. The fabric and casting material is similar to that described above. Molds of the soles of the feet may be used to fit insoles, orthopaedic shoes and the like. This embodiment can be used on most body parts, i.e. breast, face, hands, feet, scalp, and the like. Prepackaged sheets of fabric, with and without resin, may be made and sealed in foil, plastic or the like. These may be trimmed to size as needed. Tubular material, as discussed above and as illustrated in FIGS. 1, 4, 5, and 6, can also be used to make molds of the feet (not illustrated). Tubular material may also be stretched over the foot in the manner of a "slipper" to form a mold thereof (not illustrated).

The device described above may also have detackifier added to the casting resin (see: U.S. Pat. No. 5,061,555 which is incorporated herein by reference). Color may be used in the casting resin or in the substrate if desired (see: U.S. Pat. Nos. 5,061,555; 4,934,356; 5,005,566; (Ser.No. 07/705,934—all of which are commonly assigned and all of which are incorporated herein by specific reference).

Once a mold is made of any body part it may then be stored indefinitely. In practice, the mold (which is a negative impression of the body part) is usually employed to make a positive cast of the part molded. This can be done by filling the mold with plaster of Paris, or other suitable material. For amputation stumps this positive cast is then used to made a prosthesis for the amputated part, with the cast acting as a template to fit and size the proximal part of the prosthesis so that it will fit correctly on the amputation stump.

While the invention has been described with a certain degree of particularity it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A mold of a human or animal body part, comprising:
    a skin contact layer of material adapted to be positioned adjacent to said body part, said skin contact layer having spaces penetrable and wettable by a water activated resin, said resin being substantially foamable;
    a casting layer comprising a stretchable support fabric impregnated with said water activated resin, said casting layer and resin, when water activated, being applied over and in contact with said skin contact layer such that the spaces of said skin contact layer are penetrable by said resin into contact with said body part so that the skin contact layer and the casting layer along with a substantially foamed resin component form a unitary mold of said body part as the resin cures.

2. The mold of claim 1 wherein said skin contact layer is a dry knit stretchable fabric.

3. The mold of claim 1 wherein said casting resin is a isocyanate polymer compound that will foam when wetted.

4. The method of making a mold of a human or animal body part, comprising the steps of:
    placing a dry resin penetrable and wettable knit stretchable fabric over said body part and smoothing it snugly thereon;
    wetting a knit fabric substrate impregnated with a water activated foamable casting resin;
    molding at least one layer of said wet impregnated casting substrate over said dry knit fabric so as to conform to said underlying body part and forcing said wet foaming casting resin to wet and penetrate into contact with said body part the knit stretchable fabric;
    allowing said wet substrate and knit stretchable fabric to cure as a substantially foamed resin component to form a unitary mold in conformity with said body part; and
    removing said cured mold from the human or animal body part.

5. A method for making a mold of a human or animal amputation stump, comprising the steps of:
    placing a dry resin penetrable and wettable tubular stocking, closed at one end, and formed of stretchable knit fabric over said stump forming a skin contact layer;
    smoothing said stocking on said stump, to exclude any wrinkles, and closely conforming said stocking to the surface of said stump;
    wetting a tubular knit stretchable substrate, closed at one end, and impregnated with a water activated foamable casting resin forming a casting layer;
    sliding said casting layer of said wet tubular substrate impregnated with said foamable casting resin over said stocking so the stocking is wetted with resin;
    molding said wet casting layer firmly over said stocking conforming to said underlying stump and thereby forcing wet foaming casting resin through interstices of said stocking and into contact with said body part;
    allowing said resin to cure as a hardened substantially foamed resin component to form a unitary mold of said amputation stump; and removing the mold from said amputation stump.

6. A device for making a mold of an amputation stump comprising:
    a resin penetrable and wettable skin contact layer comprised of dry stretchable tubular knit fabric closed at one end and sized to fit over said amputation stump;
    at least one casting layer comprising a stretchable tubular knit fabric closed at one end, and impregnated with water activated substantially foamable casting resin and sized to fit over said skin contact layer when on said amputation stump so that the resin penetrates through the skin contact layer into contact with said body part causing the skin contact layer and the casting layer to form a unitary mold of a substantially foamed resin component when the resin cures.

* * * * *